Feb. 11, 1958 E. S. BOERNER Plant Pat. 1,682
ROSE PLANT
Filed Feb. 27, 1957
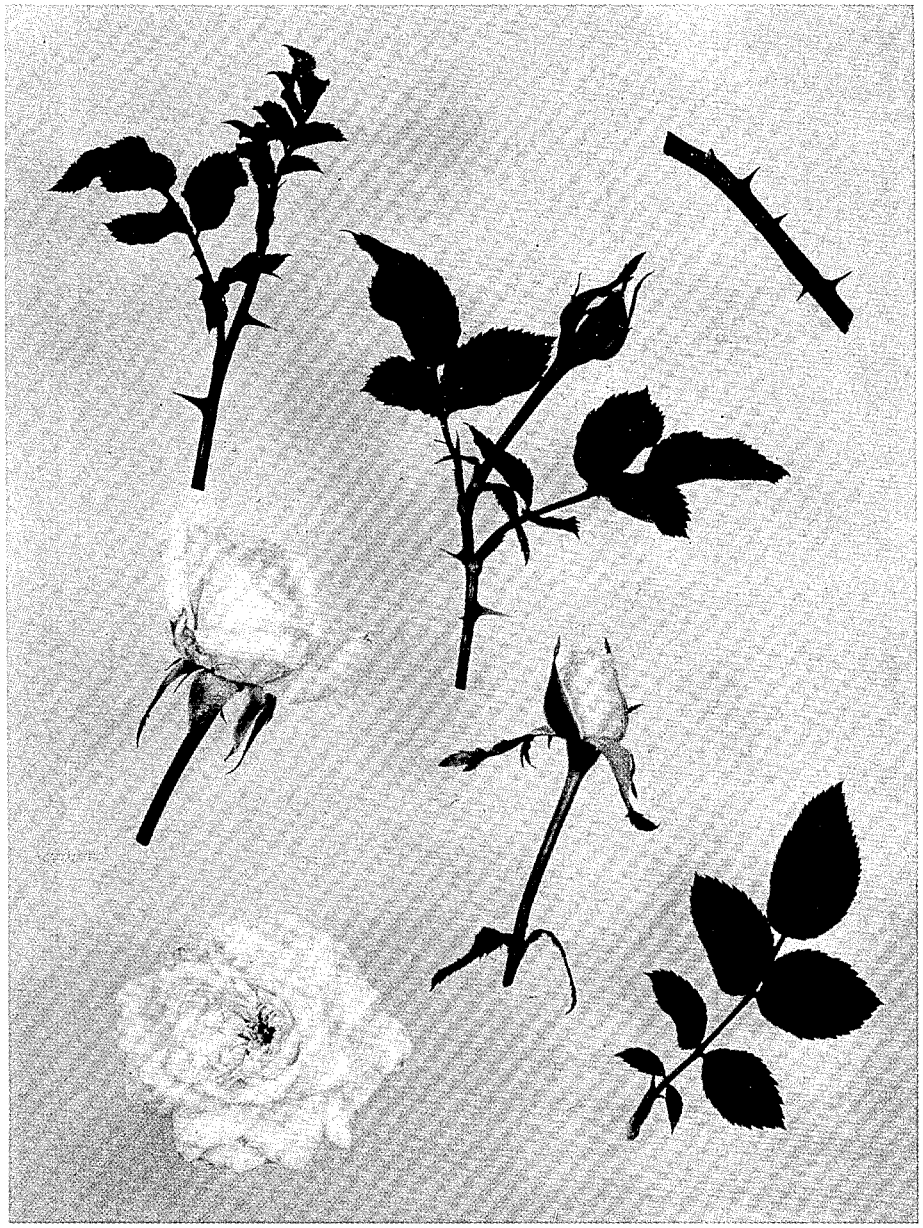
INVENTOR
E. S. Boerner
BY Robb & Robb
ATTORNEYS United States Patent Office Plant Pat. 1,682

Patented Feb. 11, 1958

1,682

ROSE PLANT

Eugene S. Boerner, Newark, N. Y., assignor, by mesne assignments, to C. W. Stuart & Co., Newark, N. Y., a corporation of New York Application February 27, 1957, Serial No. 642,920

1 Claim. (Cl. 47—61)

The present invention relates to a new and distinct variety of rose plant of the large-flowered polyantha class, which was originated by me by crossing the variety "Golden Glow" (Plant Patent No. 263) with the variety "Goldilocks" (Plant Patent No. 672).

As the result of this breeding, I have produced a new rose variety which is particularly distinct from all others of this class by reason of its low-growing, bushy and spreading habits of growth, with horizontal and pendulous branches, as compared with the typical upright growth of floribunda roses.

In addition to the unique growth characteristics referred to above, the new variety is also characterized as to novelty by the following combination of outstanding features:

(1) The new growth is distinctively and attractively edged with red coloring;

(2) The foliage is a dark, glossy, green color which contrasts in an attractive manner with the light yellow flowers;

(3) The foliage is highly resistant to blackspot and mildew;

(4) The flowers are a clear yellow color which holds well throughout the life of the flowers;

(5) The flowers are fully double in form so that the stamen and pistils rarely show; and (6) The peduncles are a brilliant red color.

The foregoing characteristics definitely differentiate my new variety from its parents, as well as from all other varieties of which I am aware.

Asexual reproduction of the new variety by budding, as performed at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color.

The following is a detailed description of the new variety, with color terminology in accordance with the Horticultural Color Chart issued by the British Color Council in collaboration with the Royal Horticultural Society, except where general color terms of ordinary dictionary significance are obvious:

Type: Hardy; dwarf; outdoor; seedling; for garden decoration.

Class: Large-flowered polyantha.

Breeding: Seedling.

*Seed parent.*—"Golden Glow."

*Pollen parent.*—"Goldilocks."

Propagation: Holds its distinguishing characteristics through succeeding propagations by budding.

*Flower*

Locality where grown and observed: Newark, New York, and Tyler, Texas.

Flowers borne: Several to stem; in irregular flat clusters; on strong stems of medium length.

Quantity of bloom: Abundant, outdoors.

Continuity: Continuous.

Fragrance: Slight.

Bud:

*Peduncle.*—Medium length; heavy; stiff; entirely smooth. Color—green, marked with Pansy Purple, Plate 928/1, page 177.

*Before calyx breaks.*—Size—small. Form—short; globular; with foliaceous appendages on the surface of the bud; with cut foliaceous parts extending beyond the tip of the bud equal to ½ or more of its length. Color—Agathia Green, Plate 60, page 60.

*As calyx breaks.*—Color—Uranium Green, Plate 63, page 63.

*As first petal opens.*—Size—medium. Form—globular. Color: outside—Sulphur Yellow, Plate 1/2, page 1; inside—Sulphur Yellow, Plate 1/2, page 1.

*Opening.*—Opens up well.

Bloom:

*Size (when fully open).*—From 2 to 2½ inches.

*Petalage.*—Very double; from 50 to 60 petals; arranged regularly.

*Form.*—Open-cupped, full, and globular at first, but becomes globular; petals being at first loosely rolled outward, but becoming tightly rolled outward at maturity.

Petals:

*Texture.* — Leathery. Inside—satiny. Outside—satiny.

*Shape.*—Outside—ovate, with apex flat, and with one notch. Intermediate—ovate, with apex flat, and with one notch. Inside—lanceolate, with one notch.

This description of a newly opened flower was made from a rose grown outdoors in the month of November, at Tyler, Texas:

*Color.*—Outer petal: outside surface — Primrose Yellow, Plate 601/3, page 65; inside surface—Primrose Yellow, Plate 601/3, page 65. Intermediate petal: outside surface—Primrose Yellow, Plate 601/2, page 65; inside surface—Primrose Yellow, Plate 601/2, page 65. Inner petal: outside surface—Primrose Yellow, Plate 601, page 65; inside surface—Primrose Yellow, Plate 601, page 65.

This description was made from a rose that was open for five days outdoors in the month of November, at Tyler, Texas:

*Color.* — Outer petal: outside surface—Primrose Yellow, Plate 601/2, page 65; inside surface—Primrose Yellow, Plate 601/2, page 65. Inner petal: outside surface—Primrose Yellow, Plate 601/2, page 65; inside surface—Primrose Yellow, Plate 601/2, page 65.

*General color effect.*—Newly opened flower—Primrose Yellow, Plate 601/2, page 65. Three days open—Primrose Yellow, Plate 601/2, page 65.

*Behavior.*—Some persist; fading brown; does not seem to be affected by adverse weather conditions.

*Flower longevity.*—On bush in garden—4 or 5 days in November. Cut roses grown outdoors and kept at living room temperatures—3 or 4 days in November.

*Reproductive organs*

Stamens: Few; irregularly arranged about pistils; mixed with petaloids.
Filaments (threads): Short; most with anthers. Color—Straw Yellow, Plate 604, page 67.
Anthers: Medium size; all open at once. Color—Straw Yellow, Plate 604, page 67.
Pollen: Very sparse.
Pistils: Many.
Styles: Uneven; medium length; thin; loosely separated.
Stigma: Color—Yellow.
Ovaries: All enclosed in calyx.
Hips: None.
Seeds: None.

*Plant*

Foligae:
*Leaves.*—Compound of 5 leaflets; abundant; small; very heavy; leathery; glossy; wrinkled.
*Leaflets.*—*Shape*—Oval, with apex obtuse. Base—obtuse. Margin—doubly serrate.
*Color.* — Mature: upper surface—near Spinach Green, Plate 0960, page 187; under surface—Scheele's Green, Plate 860/3, page 175, edged with Pansy Purple, Plate 928/3, page 177. Young: upper surface—Scheele's Green, Plate 860, page 175, edged with Pansy Purple, Plate 928/2, page 177; under surface—Spinach Green, Plate 0960/3, page 187.
*Rachis (the supporting stem of the compound leaf).*—Medium caliper. Upper side—grooved; hairy. Under side—smooth.
*Stipules.*—Long; with short points turning out at an angle of less than 45°.

*Disease resistance.*—Resistant to mildew and blackspot, as determined from comparison with other varieties grown under comparable conditions at Newark, New York, and Tyler, Texas.
Growth:
*Habit.*—Dwarf; sprawling; much-branched.
*Growth.*—Moderately vigorous.
*Canes.*—Medium caliper.
*Main stems.*—Color—bright green. Thorns—few; medium length; straight; with oblong base. Prickles—none. Hairs—none.
*Branches.* — Color—bright green. Thorns—few; medium length; straight; with oblong base. Prickles—none. Hairs—none.
*New shoots.*—Color—bright green, sometimes edged with red. Thorns—few; medium length; straight; with oblong base. Prickles—none. Hairs—none.

I claim:
A new and distinct variety of rose plant of the large-flowered polyantha class, substantially as herein shown and described, characterized particularly as to novelty by its low-growing, bushy and spreading habits of growth, with horizontal and pendulous branches, its red colored edging on the new growth, the dark, glossy dark green foliage, the good resistance of the foliage to blackspot and mildew, the distinctive clear yellow color of the flowers which holds well throughout the flower life, the fully double form of the flowers and their habit of rarely showing their stamen and pistils, but having their outer petals tightly rolled outward and reflexing to the stem and forming a ball-like bloom when fully open, and the brilliant red color of the peduncles.

No references cited.